(12) United States Patent
Satoh (10) Patent No.: US 10,208,010 B2
(45) Date of Patent: Feb. 19, 2019

(54) CRYSTAL OF A HETEROCYCLIDENE ACETAMIDE DERIVATIVE

(71) Applicant: MOCHIDA PHARMACEUTICAL CO., LTD., Tokyo (JP)

(72) Inventor: Tsutomu Satoh, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/993,082

(22) Filed: May 30, 2018

(65) Prior Publication Data

US 2018/0346436 A1 Dec. 6, 2018

Related U.S. Application Data

(60) Provisional application No. 62/512,775, filed on May 31, 2017.

(30) Foreign Application Priority Data

May 31, 2017 (JP) ................................. 2017-108017

(51) Int. Cl.
*C07D 311/58* (2006.01)

(52) U.S. Cl.
CPC ........ *C07D 311/58* (2013.01); *C07B 2200/13* (2013.01)

(58) Field of Classification Search
CPC .................................................. C07D 311/58
USPC ....................................................... 549/407
See application file for complete search history.

(56) References Cited

U.S. PATENT DOCUMENTS

2008/0287428 A1    11/2008  Uchida et al.

FOREIGN PATENT DOCUMENTS

| JP | 6230743 B1 | 11/2017 |
|----|----|----|
| WO | WO 2007/010383 A1 | 1/2007 |

OTHER PUBLICATIONS

Radressa; "TRPV1 as a Polymodal Sensor: Potential to Discover TRPV1 Antagonists Selective for Specific Activating Modalities", Chapter 11 in TRP Channels in Drug Discovery vol. I, 2012, Springer, 221-235. (Year: 2012).*
Partial Translation—Edited by Hirayama, Yukikagoubutu Kessyou Sakusei Handbook—Genri To Know-how—(Handbook for preparing crystals of organic compounds—Principle and know-how), pp. 57-84, 2008.

(Continued)

*Primary Examiner* — Daniel R Carcanague
(74) *Attorney, Agent, or Firm* — Birch, Stewart Kolasch & Birch, LLP (57) ABSTRACT

The present invention provides a type I crystal of (E)-2-(7-trifluoromethyl-chroman-4-ylidene)-N-((7R)-7-hydroxy-5,6,7,8-tetrahydronaphthalen-1-yl)acetamide having excellent TRPV1 antagonistic activity, a drug and a pharmaceutical composition containing this crystal, and a method for producing the crystal. The present invention provides a type I crystal of (E)-2-(7-trifluoromethyl-chroman-4-ylidene)-N-((7R)-7-hydroxy-5,6,7,8-tetrahydronaphthalen-1-yl)acetamide that is excellent in at least one feature selected from the group consisting of storage stability, photostability and thermodynamic stability, that can be preferably obtained with industrially high reproducibility, yield and purity, and that is useful as a crystal of an active pharmaceutical ingredient.

10 Claims, 5 Drawing Sheets
(2 of 5 Drawing Sheet(s) Filed in Color)

(56) References Cited

OTHER PUBLICATIONS

Partial Translation—Serizawa, En/Kessyoukei No Saitekika To Kessyouka Gijyutu (Optimization of salt/crystal forms and crystallization techniques therefor), Pharm Tech Japan, vol. 18, No. 10, pp. 81-96, 2002.
International Search Report dated Jul. 24, 2018, in PCT International Application No. PCT/JP2018/020634.
Written Opinion dated Jul. 24, 2018, in PCT International Application No. PCT/JP2018/020634.
Caterina et al., "The Capsaicin receptor: a heat-activated ion channel in the pain pathway," Nature, (1997), vol. 389, pp. 816-824.
Director of Evaluation and Licensing Division at MHLW, Siniyakuhin No Kikaku Oyobi Shikenhouhou No Settei Nituite (Setting of specifications and test methods of new drugs), Notification No. 568 of Evaluation and Licensing Division, MHLW (2001).
Kojima, "Iyakuhin Kaihatsu Niokeru Kessyouseisentaku No Kouritsu Wo Mezashite (Pursuing efficiency of crystal selection in drug development)," Yakuzaigaku (Pharmaceutics) (2008), vol. 68, No. 5, pp. 344-349.
Notice of Reasons for Refusal dated Jul. 25, 2017 in Japanese Patent Application No. 2017-108017 (with English translation).
Rashid et al., "Novel Expression of Vanilliod Receptor 1 on Capsaicin-Insensitive Fibers Accounts for the Alangesic Effect of Capsaicin Cream in Neuropathic Pain," Journal of Pharmacology and Experimental Therapeutics (2003), vol. 304, No. 3, pp. 940-948.
Serizawa, "En/Kessyoukei No Saitekika To Kessyouka Gijyutu (Optimization of salt/crystal forms and crystallization techniques therefor)," Pharm. Tech. Japan (2002), vol. 18, No. 10, pp. 81-96.
STN search results on May 30, 2017, by Mochida.
Szabo et al., "Role of Transient Receptor Potential Vanilliod 1 Receptors in Adjuvant-Induced Chronic Arthritis: In Vivo Study Using Gene-Deficient Mice," Journal of Pharmacology and Experimental Therapeutics (2005), vol. 314, No. 1, pp. 111-119.
Takada, "API form screening and selection in drug discovery," Parm Stage (2007), vol. 6, No. 10, pp. 20-25.
Yukikagoubutu Kessyou Sakusei Handbook—Genri To Know-how—(Handbook for preparing crystals of organic compounds—Principle and know-how) (2008), Edited by Hirayama, pp. 57-84.

\* cited by examiner

[FIG. 1]

X-RAY POWDER DIFFRACTION PATTERN OF TYPE I CRYSTAL

[FIG. 2]

MICROSCOPIC PHOTOGRAPH OF TYPE I CRYSTAL

[FIG. 3]

FT-IR SPECTRUM DATA FOR TYPE I CRYSTAL

[FIG. 4]

DSC THERMAL ANALYSIS DATA FOR TYPE I CRYSTAL

[FIG. 5]

X-RAY POWDER DIFFRACTION PATTERN OF TYPE II CRYSTAL

[FIG. 6]

MICROSCOPIC PHOTOGRAPH OF TYPE II CRYSTAL

[FIG. 7]

FT-IR SPECTRUM DATA FOR TYPE II CRYSTAL

[FIG. 8]

DSC THERMAL ANALYSIS DATA FOR TYPE II CRYSTAL

[FIG. 9]

X-RAY POWDER DIFFRACTION PATTERN OF TYPE III CRYSTAL

CRYSTAL OF A HETEROCYCLIDENE ACETAMIDE DERIVATIVE

CROSS REFERENCE TO RELATED APPLICATIONS

This non-provisional application claims the benefit under 35 U.S.C. § 119(e) to U.S. Provisional Application No. 62/512,775, filed on May 31, 2017, and under 35 U.S.C. § 119(a) to Patent Application No. 2017-108017, filed in Japan on May 31, 2017, all of which are hereby expressly incorporated by reference into the present application.

FIELD OF THE INVENTION

The present invention relates to novel crystal forms (type I crystal, type II crystal and type III crystal) of (E)-2-(7-trifluoromethyl-chroman-4-ylidene)-N-((7R)-7-hydroxy-5,6,7,8-tetrahydronaphthalen-1-yl)acetamide (hereunder sometimes called Compound (1)), which is one of heterocyclidene acetamide derivatives that has excellent Transient Receptor Potential Vanilloid I (hereunder "TRPV1") antagonism and is useful as a preventative and/or therapeutic agent for pain and the like, to a method for producing these crystals, and to a pharmaceutical composition containing these crystals. It also relates to a process for producing a pharmaceutical composition containing these crystals, and to the use of these crystals in the manufacture of the pharmaceutical composition.

BACKGROUND ART

In studies related to the pain-producing mechanism, a receptor (TRPV1) for capsaicin, which is a main pungent taste component of chili pepper, was cloned in 1997 (Non-Patent Document 1). The TRPV1, which is a receptor that recognizes capsaicin, is widely expressed in primary sensory neurons involved in pain sensation, as well as in afferent sensory fibers including C fiber nerve endings, and many TRP family members have subsequently been cloned.

Members of the TRP family are structurally similar, having 6 transmembrane domains, and the N-terminal and C-terminal ends are located within the cell. TRPV1 allows cations such as a calcium ion and a sodium ion to flow into a cell when stimulated by capsaicin or by acid (pH 6.0 or less), heat (43° C. or more) or high osmotic pressure. Accordingly,
considering the expression sites of the TRPV1 receptor and the action of capsaicin, a marked contribution of the TRPV1 receptor to the excitement of nerve was assumed. Furthermore, contributions of TRPV1 in the living body have also been clarified in many existing reports, and in particular the involvement of TRPV1 in pain is suggested by the fact that thermal hypersensitivity due to neuropathic pain does not occur in mice in which TRPV1 is deleted (TRPV1 knockout mice), the fact that edema is suppressed in a Complete Freund's Adjuvant (CFA)-induce inflammatory pain model (Non-Patent Document 2), and the fact that the desensitization action of a previously reported TRPV1 agonist produced an analgesic effect in a neuropathic pain model and an inflammatory pain model (Non-Patent Document 3).

Called a capsaicin receptor, TRPV1 is a known target of therapies for treating pain, especially acute pain, chronic pain, neuropathic pain and visceral pain. TRPV1 is stimulated in particular by vanilloids such as capsaicin and by heat, protons and high osmotic pressure, and plays a central role in pain generation. It is also important in numerous other physiological and pathophysiological processes, and has been a target of many studies seeking therapies to treat diseases or disorders such as migraine, depression, neurodegenerative disease, cognitive disorders, anxiety, epilepsy, cough, diarrhea, pruritus, ocular pain, inflammation, cardiovascular system disorders, eating disorders, medication dependence, medication misuse and urinary incontinence and the like for example.

According to Example 71 of WO 2007/010383 (Patent Document 1), a compound (1) having excellent TRPV1 antagonism was obtained as a solid.

PRIOR ART DOCUMENT

Patent Document

[Patent Document 1] WO 2007/010383

Non-Patent Document

[Non-Patent Document 1] Caterina M J, Schumacher M A, Tominaga M, Rosen T A, Levine J D, Julius D: Nature, (389), pp. 816-824, 1997
[Non-Patent Document 2] Szabo A, Helyes Z, Sandor K, Bitte A, Pinter E, Nemeth J, Banvolgyi A, Bolcskei K, Elekes K, Szolcsanyi J: Journal of Pharmacology and Experimental Therapeutics, (314), pp. 111-119, 2005
[Non-Patent Document 3] Rashid M H, Inoue M, Kondo S, Kawashima T, Bakoshi S, Ueda H: Journal of Pharmacology and Experimental Therapeutics, (304), pp. 940-948, 2003

SUMMARY OF THE INVENTION

Problem to be Solved by the Invention

An object of the present invention is to provide, for the compound (1) having excellent TRPV1 antagonism and usefulness as a therapeutic and/or preventative agent against pain and the like, a highly pure crystal suitable as an active pharmaceutical ingredient and having at least one feature selected from the group consisting of storage stability, photostability and thermodynamic stability, and having excellent photostability in particular. Another object is to provide a producing method whereby this crystal can be provided industrially by easy methods with high reproducibility and yield. Yet another object is to provide a pharmaceutical composition with excellent stability and the like.

More specifically, having thermodynamic stability for example means that crystal polymorphic transitions in the pharmaceutical manufacturing process are prevented in advance, and the quality of the pharmaceutical ingredient and the pharmaceutical product is maintained. Having storage stability for example means that because the crystal is chemically and physically stable and not hygroscopic, its quality as a pharmaceutical ingredient is maintained within the standard for a long period of time, and it can be easily processed into a pharmaceutical product and used in pharmaceutical preparations. Moreover, having photostability for example means that when the crystal as an active pharmaceutical ingredient is exposed to light irradiation it does not undergo photodecomposition, the bioactivity of the pharmaceutical ingredient is not diminished, and therefore its bioavailability is not affected, the formulation properties of the pharmaceutical product can remain stable, and the product can potentially be stored for a long period of time.

With crystals of compounds used in pharmaceuticals, it can sometimes be difficult to obtain the same crystal form even using the same methods that yielded that form in the past due to the diversity of crystallization conditions. Therefore, there is demand for an industrially applicable crystal manufacturing method whereby a stable supply of a crystal can be obtained efficiently and reproducibly and by easy methods.

By supplying a crystal of a compound (1) such as that described above, moreover, it will also be possible to supply a highly stable pharmaceutical composition.

"Polymorphism" means that there are two or more crystal forms (crystal structures) of a substance. Different crystal forms of a specific substance are also called "polymorphs". In general, "polymorphisms" appear as differences in atomic arrangement within the crystal lattices of the various polymorphs associated either with changes in steric conformation, or with the effects of intramolecular or intermolecular interactions (particularly hydrogen binding). On the other hand, the overall outer form of a substance is called its "form", and represents the outer shape of the crystal and its surface irrespective of its internal structure. Crystals may exhibit various morphologies depending on various conditions (such as the growth rate, stirring method (speed, temperature), presence of impurities and the like).

Because the various "polymorphisms" of a substance may have different crystal lattice energies, polymorphisms in a solid state may also exhibit different physical properties (such as shape, density, melting point, color, stability, solubility, dissolution rate and the like). These physical properties may affect the stability, solubility and bioavailability (absorption effect in the body, drug action, etc.) of a specific polymorphism when it is used in a drug or pharmaceutical composition or the like, as well as the storage life, formulation properties and processing characteristics of the pharmaceutical product. Since the body absorption rate may differ depending on the polymorphism, higher or lower biological activity may be obtained in comparison with that obtained originally.

With crystal polymorphisms of pharmaceutical products, the existence of multiple polymorphisms means that polymorphic transitions may occur in the manufacturing or storage process. Moreover, if one polymorphism is more thermodynamically stable than the others it may be more suitable than the other polymorphisms during the preparation process, and therefore thermodynamic stability needs to be verified.

Means for Solving the Problem

As a result of earnest research aimed at solving these problems, the inventors succeeded in crystallizing the compound (1), and discovered the existence of three crystal forms (the three crystal forms described in this Description are called the type I crystal, type II crystal and type III crystal, and the type I crystal may also be called Form I, the type II crystal may also be called Form II and the type III crystal may also be called Form III).

It was also discovered that of the three crystal forms of the compound (1), the type I crystal may be satisfactory as an active pharmaceutical ingredient because it is thermodynamically stable, is also stable in various stability tests (long-term storage test, accelerated test, photostability test), and exhibited excellent stability in the photostability test in particular. The present invention was perfected based on these findings.

The type I crystal of the compound (1) of the present invention is a compound having TRPV1 antagonism, and has an improvement effect on diseases associated with TRPV1 (such as pain for example) by antagonizing TRPV1.

A pharmaceutical composition containing the type I crystal of the compound (1) of the present invention as an active ingredient has promise as a preventative and/or therapeutic agent for diseases associated with TRPV1.

Effects of the Invention

The type I crystal of the compound (1) of the present invention is a compound having TRPV1 antagonistic activity, has low toxicity, and is useful as a pharmaceutical product.

The type I crystal of the compound (1) of the present invention is preferably a thermodynamically stable crystal, whereby crystal polymorphic transitions in the pharmaceutical manufacturing process can be prevented in advance, and the quality of the active pharmaceutical ingredient and pharmaceutical product can be maintained.

Moreover, having storage stability preferably means that the crystal is chemically and physically stable and not hygroscopic, so that its quality as a pharmaceutical ingredient can be maintained within the standard for a long period of time, and it can be easily processed into a pharmaceutical product and used in pharmaceutical preparations.

Moreover, having superior photostability preferably means that because there is no photodecomposition or isomerization of the compound structure and no decrease in bioactivity occurs, the bioavailability of the compound is not affected, the formulation properties of the pharmaceutical product can remain stable, and long-term storage is also possible.

The method for producing the type I crystal of the compound (1) of the invention is preferably an easy and industrially applicable method whereby a highly pure type I crystal can be provided with high yield and reproducibility.

Because the type I crystal of the compound (I) of the invention is excellent in at least one feature selected from the group consisting of storage stability, photostability and thermodynamic stability, it can provide a pharmaceutical composition with excellent stability and the like.

BRIEF DESCRIPTION OF THE DRAWINGS

The patent or application file contains at least one color drawing. Copies of this patent or patent application publication with color drawing will be provided by the USPTO upon request and payment of the necessary fee.

MODE FOR CARRYING OUT THE INVENTION

The present invention relates to a type I crystal of (E)-2-(7-trifluoromethyl-chroman-4-ylidene)-N-((7R)-7-hydroxy-5,6,7,8-tetrahydronaphthalen-1-yl)acetamide (Compound (1)), and to a method of producing the crystal and a pharmaceutical composition containing the crystal. It also relates to a method for producing a pharmaceutical composition containing this crystal, and to the use of this crystal in the manufacture of the pharmaceutical composition.

Moreover, the present invention also relates to methods for producing a type II crystal and type III crystal of the Compound (1).

The present invention comprises the following embodiments [1] to [31].

In this Description, any of the crystals described in any of the embodiments [1] to [14] may also be called a "(E)-2-(7-trifluoromethyl-chroman-4-ylidene)-N-((7R)-7-hydroxy-5,6,7,8-tetrahydronaphthalen-1-yl)acetamide crystal of the invention", a "crystal of the Compound (1)" or a "crystal of the invention".

Any of the crystals described in any of embodiments [1] to [6] may also be called a "type I crystal of the invention".

Any of the crystals described in any of embodiments [7] to [11] may also be called a "type II crystal of the invention".

Any of the crystals described in any of embodiments [12] to [14] may also be called a "type III crystal of the invention".

[1] The first embodiment of the invention is a type I crystal of (E)-2-(7-trifluoromethyl-chroman-4-ylidene)-N-((7R)-7-hydroxy-5,6,7,8-tetrahydronaphthalen-1-yl)acetamide, having characteristic peaks at least at diffraction angles (2θ) of about 7.9, about 10.3, about 15.8, about 16.4, about 17.2, about 19.5, about 19.9, about 21.6, about 23.9, about 25.0 and about 26.7 (°) in x-ray powder diffraction.

[1-1] The embodiment 1-1 of the invention is a type I crystal of (E)-2-(7-trifluoromethyl-chroman-4-ylidene)-N-((7R)-7-hydroxy-5,6,7,8-tetrahydronaphthalen-1-yl)acetamide, having characteristics peaks at diffraction angles (2θ) of about 7.9, about 8.9, about 10.3, about 12.0, about 15.8, about 16.4, about 17.2, about 17.6, about 18.3, about 19.5, about 19.9, about 20.8, about 21.6, about 23.9, about 24.6, about 25.0, about 26.3, about 26.7, about 27.7, about 28.6, about 29.5, about 31.4, about 32.4, about 33.2, about 33.8 and about 34.8 (°) in x-ray powder diffraction.

Figure 1:
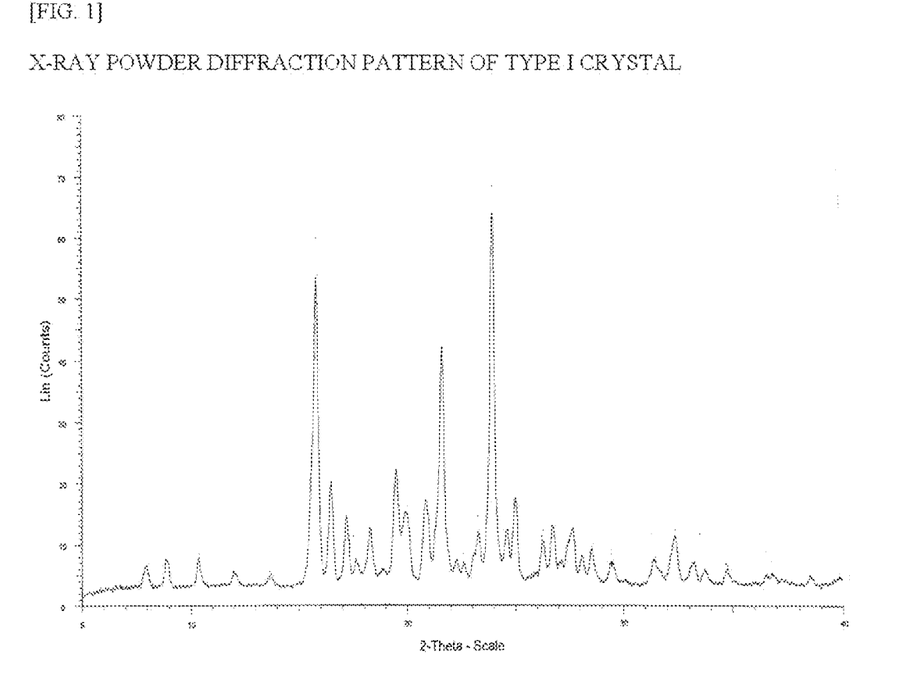
FIG. 1 is an x-ray powder diffraction pattern of the type I crystal of the Compound (I) of Example 1.

[2] The second embodiment of the invention is a type I crystal of (E)-2-(7-trifluoromethyl-chroman-4-ylidene)-N-((7R)-7-hydroxy-5,6,7,8-tetrahydronaphthalen-1-yl)acetamide, characterized by an x-ray powder diffraction pattern shown in FIG. 1.

[3] The third embodiment of the invention is a type I crystal of (E)-2-(7-trifluoromethyl-chroman-4-ylidene)-N-((7R)-7-hydroxy-5,6,7,8-tetrahydronaphthalen-1-yl)acetamide, having the diffraction angles (2θ) and relative intensities (%) shown in Tables 2 or 3 in x-ray powder diffraction.

[4] The fourth embodiment of the invention is a type I crystal of (E)-2-(7-trifluoromethyl-chroman-4-ylidene)-N-((7R)-7-hydroxy-5,6,7,8-tetrahydronaphthalen-1-yl)acetamide, and preferably the type I crystal according to any one of the embodiments [1] to [3] above, characterized by having an extrapolated melting point onset temperature of 232° C. in differential scanning calorimetry measurement (DSC measurement).

Figure 3:
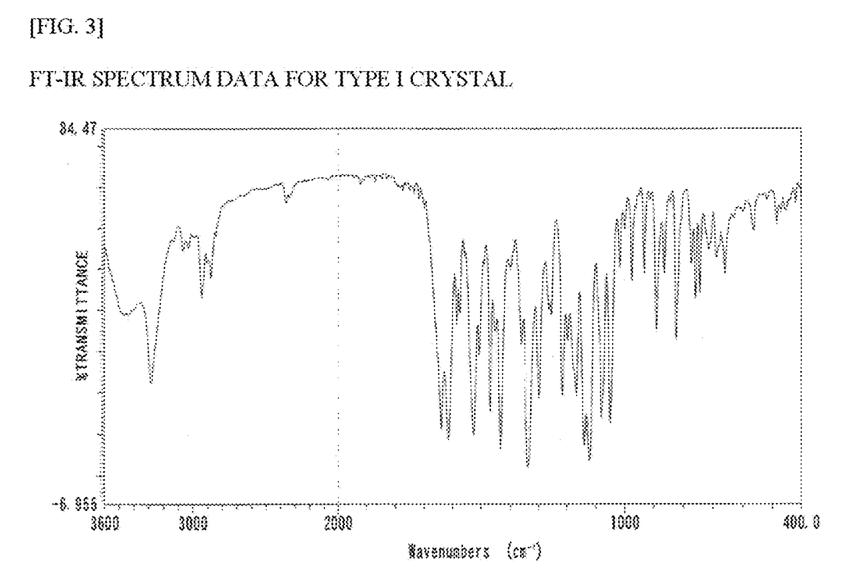
FIG. 3 shows FT-IR spectrum data for the type I crystal of the Compound (1) of Example 1.

[5] The fifth embodiment of the invention is a type I crystal of (E)-2-(7-trifluoromethyl-chroman-4-ylidene)-N-((7R)-7-hydroxy-5,6,7,8-tetrahydronaphthalen-1-yl)acetamide, and preferably the type I crystal according to any one of the embodiments [1] to [4] above, characterized by an FT-IR spectrum diagram shown in FIG. 3 and/or the data values ($cm^{-1}$) given in Table 4.

[6] The sixth embodiment of the invention is the type I crystal according to any one of embodiments [1] to [5] above, having a needle-shaped crystal morphology.

[7] The seventh embodiment of the invention is a type II crystal of (E)-2-(7-trifluoromethyl-chroman-4-ylidene)-N-((7R)-7-hydroxy-5,6,7,8-tetrahydronaphthalen-1-yl)acetamide, having characteristic peaks at least at diffraction angles (2θ) of about 10.5, about 12.2, about 12.7, about 16.1, about 17.1, about 18.4, about 19.1, about 20.6, about 22.4 and about 23.8 (°) in x-ray powder diffraction.

Figure 5:
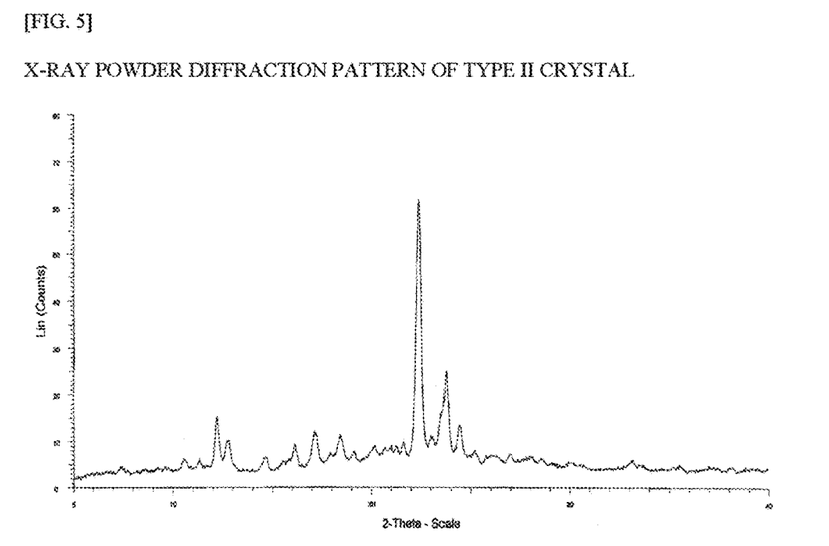
FIG. 5 is an x-ray powder diffraction pattern of the type II crystal of the Compound (1) of Example 3.

[8] The eighth embodiment of the invention is a type II crystal of (E)-2-(7-trifluoromethyl-chroman-4-ylidene)-N-((7R)-7-hydroxy-5,6,7,8-tetrahydronaphthalen-1-yl)acetamide, characterized by an x-ray powder diffraction pattern shown in FIG. 5.

[9] The ninth embodiment of the invention is a type II crystal of (E)-2-(7-trifluoromethyl-chroman-4-ylidene)-N-((7R)-7-hydroxy-5,6,7,8-tetrahydronaphthalen-1-yl)acetamide, having the diffraction angles (2θ) and relative intensities (%) shown in Table 5 in x-ray powder diffraction.

Figure 7:
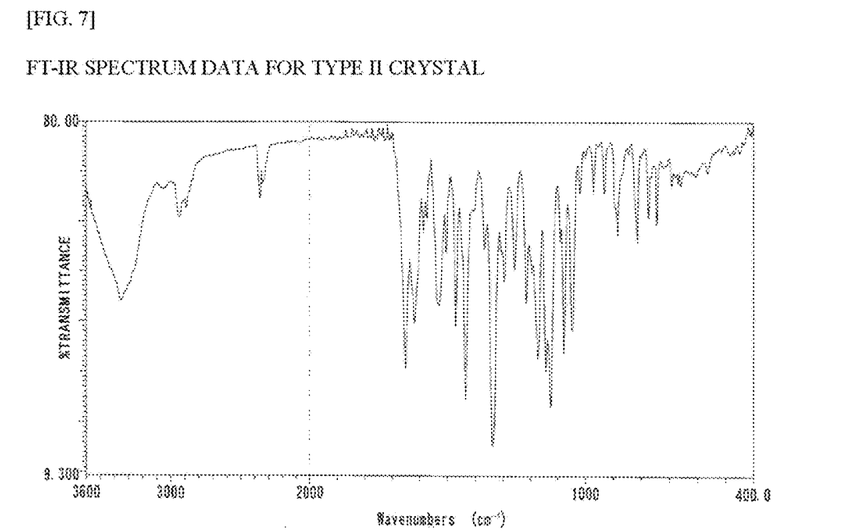
FIG. 7 shows FT-IR spectrum data for the type II crystal of the Compound (1) of Example 3.

[10] The tenth embodiment of the invention is a type II crystal of (E)-2-(7-trifluoromethyl-chroman-4-ylidene)-N-((7R)-7-hydroxy-5,6,7,8-tetrahydronaphthalen-1-yl)acetamide, and preferably the type II crystal according to any one of the embodiments [7] to [9] above, characterized by an FT-IR spectrum diagram shown in FIG. 7 and/or the data values ($cm^{-1}$) given in Table 6.

[11] The eleventh embodiment of the invention is the type II crystal according to any one of the embodiments [7] to [10] above, having a columnar crystal morphology.

[12] The twelfth embodiment of the invention is a type III crystal of (E)-2-(7-trifluoromethyl-chroman-4-ylidene)-N-((7R)-7-hydroxy-5,6,7,8-tetrahydronaphthalen-1-yl)acetamide, having characteristic peaks at diffraction angles (2θ) of about 6.9, about 13.0, about 16.6, about 17.6, about 19.9, about 20.6, about 21.3, about 22.2, about 24.0, about 27.2 and about 27.8 (°) in x-ray powder diffraction.

Figure 9:
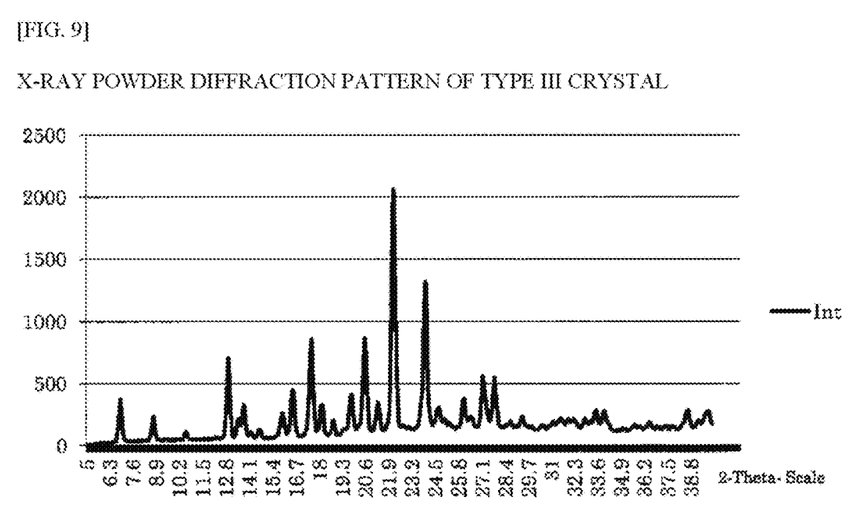
FIG. 9 is an x-ray powder diffraction pattern of the type III crystal of the Compound (1) of Example 4.

[13] The thirteenth embodiment of the invention is a type III crystal of (E)-2-(7-trifluoromethyl-chroman-4-ylidene)-N-((7R)-7-hydroxy-5,6,7,8-tetrahydronaphthalen-1-yl)acetamide, characterized by an x-ray powder diffraction pattern shown in FIG. 9.

[14] The fourteenth embodiment of the invention is a type III crystal of (E)-2-(7-trifluoromethyl-chroman-4-ylidene)-N-((7R)-7-hydroxy-5,6,7,8-tetrahydronaphthalen-1-yl)acetamide, having the diffraction angles (2θ) and relative intensities (%) shown in Table 7 in x-ray powder diffraction.

[15] The fifteenth embodiment of the invention is a method for producing the type I crystal according to any one of the embodiments [1] to [6] above, which is a method for producing the type I crystal of (E)-2-(7-trifluoromethyl-chroman-4-ylidene)-N-((7R)-7-hydroxy-5,6,7,8-tetrahydronaphthalen-1-yl)acetamide according to any one of the embodiments [1] to [6] above, comprising a step of dissolving (E)-2-(7-trifluoromethyl-chroman-4-ylidene)-N-((7R)-7-hydroxy-5,6,7,8-tetrahydronaphthalen-1-yl)acetamide under heating with a solvent selected from alcohol solvents, and mixed solvents of alcohol solvents and acetone, adding water under heating and stirring, and then cooling the mixed solution containing water with stirring to room temperature to obtain crystals.

[15-1] The solvent in the embodiment [15] above is preferably a mixed solvent of an alcohol solvent and acetone.

[15-2] The alcohol solvent in the embodiment [15] or [15-1] above is preferably methanol, ethanol or 2-propanol, or more preferably methanol or ethanol, or still more preferably ethanol.

[15-3] The mixing ratio of the mixed solvent of an alcohol solvent and acetone in the producing method according to any one of the embodiments [15] to [15-2] above is selected appropriately from the range of 1:9 to 9:1 (volume:volume, v/v). More specifically, the ratio may be ethanol:acetone=1:1 to 3:7 or the like. The ratio of the amount of water used together with this mixed solvent is mixed solvent:water=3:1 to 2:1. Part of the mixed solvent may also be mixed with the water and used. For example, assuming a ratio of mixed solvent:water=20:10, the compound may be dissolved under heating with 15 parts of the mixed solvent, and 5 parts of the mixed solvent may then be mixed and used appropriately with the 10 parts of water. The amount of the mixed solvent that is used is about 10 mL per 1 g (as solids) of the compound to be dissolved.

[15-4] The water in the producing method according to any one of the embodiments [15] to [15-3] above is preferably added gradually rather than all at once. The dropping rate is not particularly limited.

[15-5] The cooling time to room temperature in the embodiment [15] above is not particularly limited as long as it is enough time to restore the temperature of the solvent to room temperature.

[16] The sixteenth embodiment of the invention is a method for producing the type II crystal according to any one of the embodiments [7] to [11] above, which is a method for producing the type II crystal of (E)-2-(7-trifluoromethyl-chroman-4-ylidene)-N-((7R)-7-hydroxy-5,6,7,8-tetrahydronaphthalen-1-yl)acetamide according to any one of the embodiments [7] to [11] above, comprising a step of dissolving (E)-2-(7-trifluoromethyl-chroman-4-ylidene)-N-((7R)-7-hydroxy-5,6,7,8-tetrahydronaphthalen-1-yl)acetamide at room temperature with a solvent selected from ester solvents, alcohol solvents and mixed solvents of ester solvents and alcohol solvents, and then concentrating under reduced pressure to obtain crystals.

[17] The seventeenth embodiment of the invention is a method for producing the type III crystal according to any one of the embodiments [12] to [14] above, which is a method for producing the type III crystal of (E)-2-(7-trifluoromethyl-chroman-4-ylidene)-N-((7R)-7-hydroxy-5,6,7,8-tetrahydronaphthalen-1-yl)acetamide according to any one of the embodiments [12] to [14] above, comprising either a step of dissolving (E)-2-(7-trifluoromethyl-chroman-4-ylidene)-N-((7R)-7-hydroxy-5,6,7,8-tetrahydronaphthalen-1-yl)acetamide at room temperature in a polar solvent and then adding a mixed solvent of water and a polar solvent under stirring at room temperature, or a step of dissolving under heating in isopropanol, and then leaving the mixture to cool.

[18] The eighteenth embodiment of the invention is a pharmaceutical composition containing the crystal according to any one of the embodiments [1] to [14] above as an active ingredient.

[18-1] The crystal of the embodiment [18] above is preferably the type I crystal according to any one of the embodiments [1] to [6] above.

[19] The nineteenth embodiment of the invention is a medicine for treating at least one medical condition selected from the group consisting of acute pain; chronic pain; neuropathic pain; postherpetic neuralgia; trigeminal neuralgia; lower-back pain; pain after spinal cord injury; leg pain; causalgia; diabetic neuralgia; pain caused by edema, burns, sprains, bone fractures, and the like; pain after surgical operations; scapulohumeral periarthritis; osteoarthritis; arthritis; rheumatic arthritis pain; inflammatory pain; cancer pain; migraines; headaches; toothaches; neuralgia; muscle pain; hyoeralgesia; pain caused by angina pectoris, menstruation, and the like; neuropathy; nerve damage; neurodegeneration; chronic obstructive pulmonary disease (COPD); asthma; airway hypersensitivity; stridor; cough; rhinitis; inflammation of mucosa such as eyes; nervous dermatitis; inflammatory skin complaint such as psoriasis and eczema; edema; allergic diseases; gastroduodenal ulcer; ulcerative colitis; irritable colon syndrome; Crohn disease; urinary incontinence; urinary urge incontinence; overactive bladder; cystitis; nephritis; pancreatitis; uveitis; splanchnopathy; ischemia; apoplexy; dystonia; obesity; septicemia; and pruritus, which is a pharmaceutical composition containing the crystal according to any one of the embodiments [1] to [14] above as an active ingredient in an amount effective for treating that diseases.

[19-1] The crystal in the embodiment [19] above is preferably the type I crystal according to any one of the embodiments [1] to [6].

Unless otherwise specified, "treating" as in "treating a disease" in this Description means to cause recovery in or to alleviate or suppress a "disease" or one or more "diseases".

Depending on the condition of the patient, "preventing" in this Description means preventing the occurrence of a "disease" or preventing the occurrence of any symptoms associated with that "disease". It encompasses not only preventing a "disease", but also reducing the severity of the "disease" before it occurs or reducing the severity of any symptoms thereof.

[20] The twentieth embodiment of the invention is the pharmaceutical composition for treating at least one disease of the nineteenth embodiment of the invention, containing the crystal according to any one of the embodiments [1] to [14] above as an active ingredient in an amount effective for antagonizing TRPV1.

[20-1] The crystal of the embodiment [20] above is preferably the type I crystal according to any one of the embodiments [1] to [6] above.

[21] The twenty-first embodiment of the invention is a preventative and/or therapeutic agent for at least one condition selected from the conditions described in the nineteenth embodiment of the invention, containing the crystal according to any one of the embodiments [1] to [14] above as an active ingredient.

[21-1] The embodiment [21] above is preferably a preventative and/or therapeutic agent for a pain condition, containing the crystal according to any one of the embodiments [1] to [14] above as an active ingredient.

[21-2] The crystal in the embodiments [21] and [21-1] above is preferably the type I crystal according to any one of the embodiments [1] to [6] above.

[22] The twenty-second embodiment of the invention is a therapeutic agent for at least one disease selected from the diseases described in the nineteenth embodiment of the invention, containing the crystal according to any one of the embodiments [1] to [14] as an active ingredient.

[22-1] The embodiment [22] above is preferably a therapeutic agent for a pain condition, containing the crystal according to any one of the embodiments [1] to [14] above as an active ingredient.

[22-2] The crystal in the embodiments [22] and [22-1] above is preferably the type I crystal according to any one of the embodiments [1] to [6] above.

[23] The twenty-third embodiment of the invention is a preventative and/or therapeutic agent for a disease associated with TRPV1, characterized by containing the crystal according to any one of the embodiments [1] to [14] above as an active ingredient.

[23-1] The crystal in the embodiment [23] above is preferably the type I crystal according to any one of the embodiments [1] to [6] above.

[24] The twenty-fourth embodiment of the invention is a therapeutic agent for a disease associated with TRPV1, characterized by containing the crystal according to any one of the embodiments [1] to [14] above as an active ingredient.

[24-1] The crystal of the embodiment [24] above is preferably the type I crystal according to any one of the embodiments [1] to [6] above.

[25] The twenty-fifth embodiment of the invention is a TRPV1 antagonist that is a pharmaceutical composition containing the crystal according to any one of the embodiments [1] to [14] above as an active ingredient.

[25-1] The crystal in the embodiment [25] above is preferably the type I crystal according to any one of the embodiments [1] to [6] above.

[26] The twenty-sixth embodiment of the invention is the use of the crystal according to any one of the embodiments [1] to [14] above as a pharmaceutical composition.

[26-1] The crystal in the embodiment [26] above is preferably the type I crystal according to any one of the embodiments [1] to [6] above.

[27] The twenty-seventh embodiment of the invention is the use of the crystal according to any one of the embodiments [1] to [14] above in the manufacture of a pharmaceutical composition.

[27-1] The crystal in the embodiment [27] above is preferably the type I crystal according to any one of the embodiments [1] to [6] above.

[28] The twenty-eighth embodiment of the invention is the use of the crystal according to any one of the embodiments [1] to [14] above as a TRPV1 antagonist.

[28-1] The crystal in the embodiment [28] above is preferably the type I crystal according to any one of the embodiments [1] to [6] above.

[29] The twenty-ninth embodiment of the invention is the use of the crystal according to any one of the embodiments [1] to [14] above in the manufacture of a TRPV1 antagonist.

[29-1] The crystal in the embodiment [29] above is preferably the type I crystal according to any one of the embodiments [1] to [6] above.

[30] The thirtieth embodiment of the invention is method for treating at least one disease selected from the group of diseases described in the nineteenth embodiment of the invention, comprising the administration of the crystal according to any one of the embodiments [1] to [14] above to a subject in need of treatment for that condition in an amount effective for treating the disease.

[30-1] The crystal in the embodiment [30] above is preferably the type I crystal according to any one of the embodiments [1] to [6] above.

[31] The thirty-first embodiment of the invention is method for treating at least one disease selected from the group of the diseases described in the nineteenth embodiment of the invention, comprising the administration of the crystal according to any one of the embodiments [1] to [14] above to a subject in need of treatment for that condition in an amount effective for antagonizing TRPV1.

[31-1] The crystal in the embodiment [31] above is preferably the type I crystal according to any one of the embodiments [1] to [6] above.

The TRPV1 antagonistic activity of the crystal according to any one of embodiments [1] to [14] of the invention can be measured by appropriately selected methods, such as those of the Pharmacological Experimental Example 1 below (human-derived TRPV1 antagonistic activity).

The crystal according to any one of embodiments [1] to [14] of the invention has excellent TRPV1 antagonist activity in Pharmacological Experimental Example 1 (human TRPV1 antagonistic activity).

The present invention is explained in detail below.

All of the crystal forms of the crystals of (E)-2-(7-trifluoromethyl-chroman-4-ylidene)-N-((7R)-7-hydroxy-5,6,7,8-tetrahydronaphthalen-1-yl)acetamide in the present invention are not hydrates, or in other words are anhydrides.

All of the crystal forms of the crystal of (E)-2-(7-trifluoromethyl-chroman-4-ylidene)-N-((7R)-7-hydroxy-5,6,7,8-tetrahydronaphthalen-1-yl)acetamide in the present invention may also be deuterated.

In this Description, methods of crystal analysis by x-ray diffraction are generally used to analyze the resulting crystals. Mechanical methods or optical methods (such as the FT-Raman spectrum or solid NMR spectrum methods) or the like may also be used for determining the crystal orientations. Thermal analysis of the crystals (differential scanning calorimetry (DSC)), infrared absorption spectrum (IR) analysis (KBr method, solvent method) and the like may also be performed by ordinary methods.

By their nature, the spectral peaks obtained by these analysis methods inevitably contain certain measurement errors. Those having spectral peak values within the error ranges are also included in the crystal of the invention.

With respect to the diffraction angles (2θ) of x-ray powder diffraction for example, different samples of a specific crystal form will share the same principal peaks at the same diffraction angles (2θ), but differences in secondary peaks may occur in the x-ray powder diffraction pattern. This means that errors of "±0.2" or "±0.1" in the diffraction angles (2θ) are allowable in x-ray powder diffraction. In general, the diffraction angles in x-ray powder diffraction (2θ) are liable to errors in the range of ±0.2°. Consequently, unless otherwise specified, a "diffraction angle (2θ) of (about) X°" in the present invention signifies a diffraction angle (2θ) of ((X−0.2) to (X+0.2)°). Not only crystals that exactly match the diffraction angle in x-ray powder diffraction, but crystals that match the diffraction angle within an error range of ±0.2° are included in the present invention.

A "characteristic peak" at a diffraction angle (2θ) in x-ray powder diffraction in this Description means a peak of maximum absorption at a diffraction angle (2θ) with a value listed in Tables 2, 3, 5 or 7. The relative intensity (%) at particular diffraction angle (2θ) in x-ray powder diffraction may differ depending on the measurement conditions because the intensity of the x-rays at each peak may change or may not appear at all in some cases depending on the size and direction of the crystals.

Errors of "±0.2" or "±0.1" are allowable with respect to infrared absorption ($cm^{-1}$) in the FT-IR spectrum, and errors of "±1" are allowable in the DSC measurement temperature (° C.).

The type I crystal of the invention is characterized by having an extrapolated melting point onset temperature of 232° C. in differential scanning calorimetry measurement (DSC measurement) under the condition of temperature rise rate of 10° C./min.

The type II crystal of the invention is characterized in that some heat absorption can be confirmed near 170° C. to 200° C. in DSC measurement, the change in crystal form is confirmed under a microscope, a transition to the type I crystal is observed, and the extrapolated melting point onset temperature is near the melting point of the type I.

The type III crystal of the invention is characterized in that a transition to the type I crystal is observed near 170° C. during temperature rise in x-ray powder diffraction under temperature variable conditions.

The type I crystal of (E)-2-(7-trifluoromethyl-chroman-4-ylidene)-N-((7R)-7-hydroxy-5,6,7,8-tetrahydronaphthalen-1-yl)acetamide of the invention can be manufactured by causing a transition in a crystal (e.g., a type II crystal and/or type III crystal) of (E)-2-(7-trifluoromethyl-chroman-4-ylidene)-N-((7R)-7-hydroxy-5,6,7,8-tetrahydronaphthalen-1-yl)acetamide, which comprises multiple crystal morphologies. For example, a transition from a type II crystal or type III crystal to a type I crystal can be caused by heating the crystal at a temperature of at least 170° C.

In this Description, crystal transition is a phenomenon whereby a crystal structure changes when heat or pressure is applied.

Examples of "crystal transition methods" include methods that are known per se, such as for example methods of crystallization from solution (such as concentration methods, slow cooling methods, reaction methods (diffusion method, electrolysis method), hydrothermal growth methods and fusing agent methods), methods of crystallization from vapor (such as gasification methods (sealed tube method, gas steam method), gas phase reaction methods and chemical transportation methods), methods of crystallization from melt (such as normal freezing methods (pulling up method, temperature gradient method, Bridgman method), zone melting methods (zone leveling method, float zone method) and special growth methods (VLS method, liquid phase epitaxy)), transpiration methods (methods of dissolving crystals in a solvent, filtering and evaporating the solvent under atmospheric conditions), slurry methods (methods of adding crystals to a solvent so that an excess of the solid remains to make a suspension, and stirring at atmospheric temperature or under heating and cooling to collect a solid by filtration), and vacuum drying, trituration, pulverization, pressurization and the like.

In the method for producing a type I crystal of the invention (embodiment [15] above), the alcohol solvent in the solvent used to obtain the type I crystal is preferably methanol, ethanol or 2-propanol, or more preferably methanol or ethanol, or still more preferably ethanol.

In the method for producing a type I crystal of the invention (embodiment [15] above), a mixed solvent of an alcohol solvent and acetone is preferred as the solvent used to obtain the type I crystal. Examples include alcohol solvents such as methanol or ethanol, and mixed solvents of alcohol solvents with acetone. A mixed solvent of ethanol and acetone is preferred from the standpoint of solubility and yield.

In the method for manufacturing a type I crystal of the invention (embodiment [15] above), the mixing ratio of the mixed solvent of an alcohol solvent and acetone can be selected appropriately within the range of 1:9 to 9:1 (volume:volume, v/v). More specifically, the ethanol:acetone ratio may be 1:1, 3:7 or the like. For the ratio of the amount of water used with this mixed solvent, the mixed solvent: water ratio is 3:1 to 2:1. Part of the mixed solvent may also be used in a mixture with water. For example, if the ratio of mixed solvent:water is 20:10, the compound may be dissolved under heating with 15 parts of the mixed solvent, and 5 parts of the mixed solvent may then be mixed and used appropriately with the 10 parts of water. The amount of the mixed solvent that is used is about 10 mL per 1 g (as solids) of the compound to be dissolved.

The water in the method for producing a type I crystal of the invention (embodiment [15] above) is preferably added gradually rather than all at once. The dropping rate is not particularly limited.

The cooling time to room temperature in the method for producing a type I crystal of the invention (embodiment [15] above) is not particularly limited as long as it is enough time to restore the temperature of the solvent to room temperature.

In the method for producing a type I crystal of the invention (embodiment [15] above), the conditions consisting of the solvent or mixed solvent used in obtaining the type I crystal, the mixing ratio of water with the solvent or mixed solvent, the amount of the mixed solvent used, the water dropping and the cooling time to room temperature may be combined and set appropriately.

In the method for producing a type II crystal of the invention (embodiment [16] above), the solvent used to obtain the type II crystal may be an ester solvent, an alcohol solvent or a mixed solvent of an ester solvent and an alcohol solvent.

For the solvent in the method for producing a type II crystal of the invention (embodiment [16] above), ethyl acetate is preferred as an ester solvent, methanol is preferred as an alcohol solvent, and a mixed solvent of ethyl acetate and methanol is especially preferred.

When using a mixed solvent of ethyl acetate and methanol in the method for producing a type II crystal of the invention (embodiment [16] above), for example the solid is first suspended in a 9:1 (volume:volume, v/v) mixed solvent of ethyl acetate:methanol at room temperature, and then methanol is added until the solid dissolves. The final ethyl acetate: methanol mixing ratio is ethyl acetate:methanol=3:1 to 4:1, or preferably 3.6:1. The amount of the mixed solvent of ethyl acetate and methanol that is used is about 40 to 50 mL per 1 g of the solids amount of the compound to be dissolved.

In the method for producing a type II crystal of the invention (embodiment [16] above), the conditions consisting of the solvent or mixed solvent used in obtaining the type II crystal, the mixing ratio of the mixed solvent and the amount of the mixed solvent used may be combined and set appropriately.

The polar solvent in the method for producing a type III crystal of the invention (embodiment [17] above) is preferably dimethylsulfoxide. The ratio of the polar solvent to the mixed solvent of a polar solvent and water is preferably 1:2. The mixed solvent of a polar solvent and water is preferably a mixed solvent of dimethylsulfoxide and water, and the mixing ratio (volume:volume, v/v) of dimethylsulfoxide to water is preferably 1:1 to 1:2, or more preferably 1:2. The added amounts of dimethylsulfoxide and water are preferably 1 to 2 times, or more preferably 1.5 times the volume of dimethylsulfoxide used to dissolve the solid. The initial amount of dimethylsulfoxide used to dissolve the solid is about 10 mL per 1 g of the solids amount of the compound to be dissolved.

In the method for producing a type III crystal of the invention (embodiment [17] above), the conditions consisting of the polar solvent, the mixing ratio of the polar solvent and water, the added amounts of the polar solvent and water and the initial amount of dimethylsulfoxide used to dissolve the solid when obtaining the type III crystal may be combined and set appropriately.

In the crystal producing method of the invention, crystallization is performed at a temperature of about −30° C. to 80° C., and in the case of the type I crystal it is preferably performed after the temperature has been raised from room temperature (1° C. to 30° C.) to 60° C. to 70° C. and the compound to be crystallized has been dissolved at a temperature at which the compound is completely dissolved, while in the case of the type II and type III crystals it is preferably performed at room temperature (1° C. to 30° C.).

Figure 2:
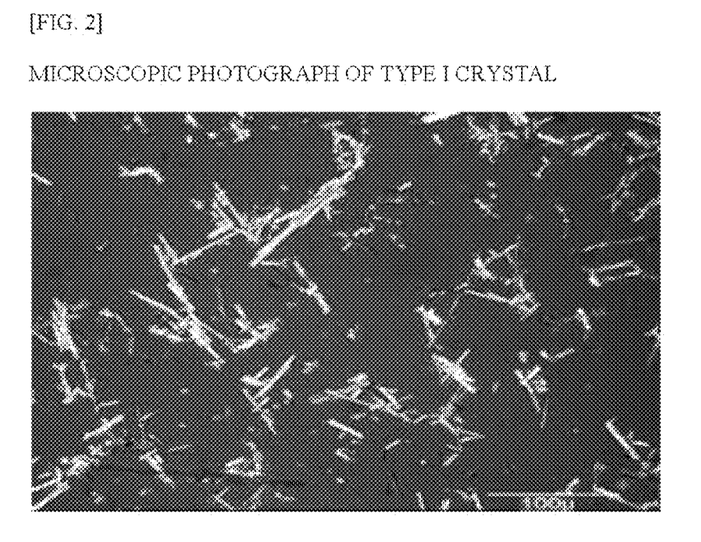
FIG. 2 is a microscopic photograph of the type I crystal of the Compound (1) of Example 1.

In the present invention, the type I crystal is obtained as needle-shaped crystals such as those shown in FIG. 2 by crystallization under particular conditions.

Figure 6:
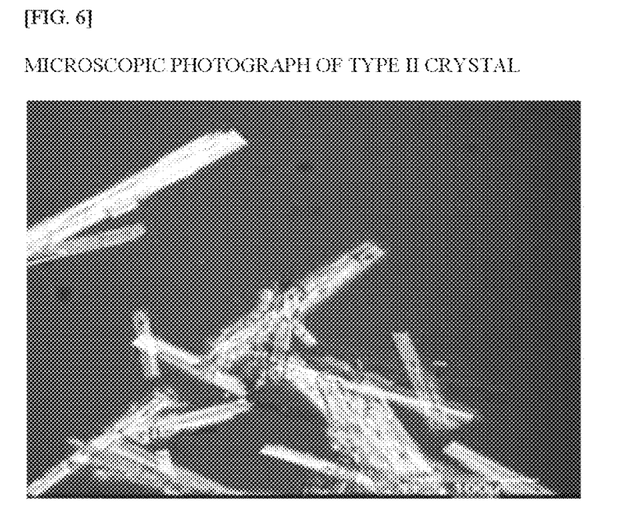
FIG. 6 is a microscopic photograph of the type II crystal of the Compound (1) of Example 3.

In the present invention, the type II crystal is obtained as columnar crystals such as those shown in FIG. 6 by crystallization under particular conditions.

However, it is understood that these morphologies may form other crystal habits under certain conditions, and such crystal habits are also included in the scope of the invention.

Unless otherwise specified, in this Description "needle-shaped" means a needle-shaped prism, and this shape is also called "needle thread-shaped"

Unless otherwise specified, in this Description "columnar" means a crystal grown parallel in a single direction and assuming a long, thin prismatic column shape.

The chemical purities of the type I crystal, type II crystal and type III crystal in the present invention are preferably about 95% to 100%, or more preferably about 97% to 100%, or still more preferably about 99% to 100%.

In the present invention, the type I crystal in particular is useful as a pharmaceutical product because it exhibits good results in at least one kind of testing selected from the group consisting of long-term storage testing, accelerated testing and other stability testing and photostability testing, and preferably has no problems of hygroscopicity.

In the present invention, the type I crystal in particular is a useful crystal because it has excellent thermodynamic stability and is therefore easy to handle, and because crystal polymorphic transitions in the pharmaceutical manufacturing process can be prevented in advance, so that the quality of the active pharmaceutical ingredient and pharmaceutical product can be maintained, and a solid pharmaceutical composition (pharmaceutical preparation) can be manufactured with high reproducibility.

In the present invention, the type I crystal in particular has extremely high chemical and physical stability, and can be used as a therapeutic and/or preventative agent for pain having TRPV1 antagonistic activity.

In this Description, "pain" is a feature of many external injuries and disease conditions. When there is actual injury to bodily tissue due to disease or external injury, the characteristics of nociceptor activation change, and this leads to hypersensitivity at the damaged site and in neighboring normal tissue. Specific examples of pain include, but are not limited to, osteoarthritis pain, arthritis pain, neuropathic pain, post-surgical pain, lower back pain, diabetic neuropathy, pain during surgery, cancer pain, chemotherapy-induced pain, headache (including cluster headache, tension headache and migraine headache), trigeminal neuraligia, Herpes zoster pain, postherpetic neuraligia, carpal tunnel syndrome, inflammatory pain, pain from rheumatoid arthritis, pain from colitis or interstitial cystitis, visceral pain, pain from kidney stones, pain from gallstones, sore throat, fibromyalgia, chronic pain syndrome, thalamic pain syndrome, pain from stroke, phantom limb pain, sunburn, radiculopathy, complex local pain syndrome, HIV sensory neuropathy, central nervous system disorder pain syndrome, multiple sclerosis pain, Parkinson's pain, pain from spinal cord injury, menstrual pain, toothache, pain from bone metastasis, pain from endometriosis, pain from uterine fibroid, nociceptive pain, hyperalgesia and pain from temporomandibular osteoarthritis and the like.

[Method for Producing (E)-2-(7-trifluoromethyl-chroman-4-ylidene)-N-((7R)-7-hydroxy-5,6,7,8-tetrahydronaphthalen-1-yl)acetamide (Compound (1))]

The Compound (1) can be produced by optical resolution of the gray solid compound (E)-2-(7-trifluoromethyl-chroman-4-ylidene)-N-(7-hydroxy-5,6,7,8-tetrahydronaphthalen-1-yl)acetamide (Compound A) obtained in Example 70 of WO 2007/010383 according to the methods described in Examples 71 and 72 of WO 2007/010383. This optical resolution can be performed appropriately by ordinary methods by a person skilled in the art using an optical preparative chromatography for example, and the conditions of optical resolution can also be set appropriately.

More specifically, the respective enantiomers of the title compound can be obtained as a first fraction (69 mg, white solid, 99.9% ee, retention time 9.9 min: Compound A-1) and a second fraction (71 mg, white solid, 99.3% ee, retention time 17.3 min: Compound A-2) by subjecting the Compound A (160 mg) to optical resolution using preparative chromatography (column: Daicel Chemical Industries, Ltd. Chiralpak AD-H, solvent: EtOH:Et$_2$NH=100:0.1).

The first fraction separated by the optical resolution column (Compound A-1) is (E)-2-(7-trifluoromethyl-chroman-4-ylidene)-N-((7R)-7-hydroxy-5,6,7,8-tetrahydronaphthalen-1-yl)acetamide (Compound (1)), while the second fraction (Compound A-2) is (E)-2-(7-trifluoromethyl-chroman-4-ylidene)-N-((7S)-7-hydroxy-5,6,7,8-tetrahydronaphthalen-1-yl)acetamide.

The structural formula for the Compound (1) is shown below.

[CHEMICAL FORMULA 1]

Compound (1)

[Combination Drugs Used with the Crystal or Pharmaceutical Composition of the Invention]

The crystal or pharmaceutical composition thereof of the invention may also be used in combination with other drugs or medicines by ordinary methods used in the pharmaceutical field. Examples of such drugs include analgesics such as opioid agonists, e.g morphine; gabapentin, pregabalin, and duloxetine, and anti-depressants such as amitriptyline; antiepileptics such as carbamazepine and phenytoin; anti-arrhythmics such as mexiletine and the like that are sometimes diverted to neuropathic pain and prescribed; and NSAIDs such as diclofenac, indomethacin, ibuprofen and naproxen, and anti-inflammatories including COX-2 inhibitors such as Celebrex. Preferred examples are morphine, gabapentin or pregabalin, diclofenac and Celebrex.

The crystal or pharmaceutical composition thereof of the invention may be used not only in combination with other drugs, but also in treatments in combination with other therapies. Specific examples include acupuncture, laser therapy, nerve block therapy and the like.

For diseases or conditions other than pain that are associated with TRPV1, the crystal of the invention or a pharmaceutical composition thereof may be used in combination with other drugs used in the corresponding field. For example, it may be combined with commonly used NSAIDs, DMARDs, TNF-α antibodies, soluble TNF-α receptors, steroids, immunosuppressants and the like in the treatment of chronic rheumatoid arthritis. It may also be combined with β-2 receptor agonists, steroids and other commonly used therapeutic drugs in the treatment of COPD and allergic conditions. It may also be combined with anticholinergics in the treatment of overactive bladder and urinary incontinence.

By using the crystal with an existing drug in the treatment of above diseases, it is possible to reduce the administered amount of the existing drug and alleviate the side effects of the existing drug. Of course, combination methods using these drugs are not limited to the diseases listed above, and the combination drugs are not limited to the compounds listed above.

When the crystal of the invention is used together with a combination drug, they may be either separate preparations or a mixture. In the case of separate preparations, they may be administered simultaneously, or administered with a staggered time.

[Pharmaceutical Composition of Crystal of Invention]

The pharmaceutical composition of the crystal of the present invention contains a crystal of (E)-2-(7-trifluoromethyl-chroman-4-ylidene)-N-((7R)-7-hydroxy-5,6,7,8-tetrahydronaphthalen-1-yl)acetamide, in combination with pharmaceutically acceptable additives.

More specifically, excipients (such as lactose, sucrose, mannitol, crystalline cellulose, silicic acid, corn starch and potato starch), binders (such as cellulose (hydroxypropyl cellulose (HPC), hydroxypropyl methylcellulose (HPMC)), crystalline cellulose, sugars (lactose, mannitol, sucrose, sorbitol, erythritol, xylitol), starches (corn starch, potato starch), pregelatinized starch, dextrin, polyvinylpyrrolidone (PVP), macrogol, and polyvinyl alcohol (PVA)), lubricants (such as magnesium stearate, calcium stearate, talc and carboxymethyl cellulose), disintegrants (such as starches (corn starch, potato starch), carboxymethyl starch sodium, carmellose, carmellose calcium, croscarmellose sodium, crospovidone), coating agents (such as cellulose (hydroxypropyl cellulose (HPC), hydroxypropyl methyl cellulose (HPMC), aminoalkyl methacrylate copolymer E and methacrylic copolymer LD), plasticizers (such as triethyl citrate and macrogol), masking agents (such as titanium oxide), colorants, perfumes, preservatives (such as benzalkonium chloride and paraoxybenzoic acid ester), isotonic agents (such as glycerin, sodium chloride, calcium chloride, mannitol and glucose), pH adjusters (such as sodium hydroxide, potassium hydroxide, sodium carbonate, hydrochloric acid, sulfuric acid, and buffers such as phosphate buffers), stabilizers (such as sugars, sugar alcohols and xanthan gum), dispersants, anti-oxidants (such as ascorbic acid, butylhydroxyanisole (BHA), propyl gallate and dl-α-tocopherol), buffers, preservatives (such as paraben, benzyl alcohol and benzalkonium chloride), aromatics (such as vanillin, 1-menthol and rose oil), solubilizing agents (such as polyoxyethylene-hardened castor oil, polysorbate 80, polyethylene glycol, phospholipid cholesterol and triethanolamine), absorption promoters (such as sodium glcyolate, sodium edetate, sodium caprate, acylcarnitines and limonene), gelling agents, suspension agents or emulsifiers, and commonly used kinds of appropriate additives and solvents may be combined appropriately with the crystal of the invention to produce various dosage forms.

Examples of various dosage forms include tablets, capsules, granules, powders, pills, aerosols, inhalants, ointments, patches, suppositories, injections, troches, liquids, spirits, suspensions, extracts, elixirs and the like. Administration to a patient may be by oral, subcutaneous, intramuscular, intranasal, transcutaneous, intravenous, intraarterial, perineural, epidural, intrathecal, intracerebroventricular, intrarectal or inhalation administration or the like.

The dose of the crystal of the invention is normally 0.005 mg to 3.0 g per adult per day, or more preferably 0.05 mg to 2.5 g, or still more preferably 0.1 mg to 1.5 g, and can be increased or decreased appropriately according to the symptoms and the administration route.

The whole dose may be administered orally or parenterally in one or two to six administrations, or may be administered continuously by intravenous drip or the like.

PHARMACOLOGICAL EXPERIMENTAL EXAMPLES

The present invention is explained in detail below using experimental examples, but the present invention is not limited by these examples.

The following Pharmacological Experimental Example 1 provides a method for testing the effectiveness of the crystal of the invention.

Pharmacological Experimental Example 1:
Measurement of Capsaicin-Induced Ca Influx in Human TRPV1-Transformed CHO Cell Line (1) Establishment of Human TRPV1-Transformed CHO Cell Line Human vanilloid receptor 1 (hTRPV1) cDNA was cloned from a human brain. The cloned hTRPV1 cDNA was inserted into a pCAGGS vector, which was then genetically introduced into a CHO-K1 cell line to transform the cells. Clones obtained by limiting dilution were stimulated with capsaicin, and clones with a high responsiveness were selected based on increased Ca concentration. The selected clones were then used for the following experiment.

(2) Measurement of Ca Influx Using FDSS-6000

Human TRPV1-transformed CHO cells were seeded at a density of 40,000 cells per well on a 96-well plate (black walls, transparent bottom/manufactured by Greiner Bio-One International GmbH). The cells was cultured overnight under conditions of 37° C., 5% $CO_2$, after which the loading solution of a FLIPR Calcium 3 assay kit (manufactured by Molecular Devices, LLC.) with 2.5 mmol/L of probenecid added thereto was added to each well in the same amount as the medium, and the cells were cultured at 37° C. for 60 minutes. Changes in intracellular Ca concentration were measured for 3 minutes after capsaicin stimulus (1 nmol/L to 1 μmol/L) with an FDSS-6000 ($\lambda$ex: 480 nm, $\lambda$em: 540 nm, Hamamatsu Photonics K.K.). The integral values of the respective intracellular Ca concentration increase rates in the medium group and the group treated with the crystal of the invention were calculated, and capsaicin concentration reaction curves were prepared. The concentration (A2 value) of the crystal of the invention that caused the capsaicin concentration reaction curve during medium group treatment to shift to the right side by two times was calculated, and the inhibitory effect of the test compound was confirmed based on this value.

The TRPV1 antagonist activity of the test compound (E)-2-(7-trifluoromethyl-chroman-4-ylidene)-N-((7R)-7-hydroxy-5,6,7,8-tetrahydronaphthalen-1-yl)acetamide was shown in Table 1 in terms of the A2 value.

TABLE 1

| Test compound | A2 value |
|---|---|
| (E)-2-(7-trifluoromethyl-chroman-4-ylidene)-N-((7R)-7-hydroxy-5,6,7,8-tetrahydronaphthalen-1-yl)acetamide | A |

(A2 value: A less than 100 nmol/L)

These results showed that the crystal of the invention had excellent TRPV1 antagonistic activity.

Thus, as an excellent TRPV1 antagonist, it is expected that the crystal of the invention will be used as a preventative and/or therapeutic agent for at least one medical condition selected from the group consisting of acute pain; chronic pain; neuropathic pain; postherpetic neuralgia; trigeminal neuralgia; lower-back pain; pain after spinal cord injury; leg pain; causalgia; diabetic neuralgia; pain caused by edema, burns, sprains, bone fractures, and the like; pain after surgical operations; scapulohumeral periarthritis; osteoarthritis; arthritis; rheumatic arthritis pain; inflammatory pain; cancer pain; migraines; headaches; toothaches; neuralgia; muscle pain; hyoeralgesia; pain caused by angina pectoris, menstruation, and the like; neuropathy; nerve damage; neurodegeneration; chronic obstructive pulmonary disease (COPD); asthma; airway hypersensitivity; stridor; cough; rhinitis; inflammation of mucosa such as eyes; nervous dermatitis; inflammatory skin complaint such as psoriasis and eczema; edema; allergic diseases; gastroduodenal ulcer; ulcerative colitis; irritable colon syndrome; Crohn disease; urinary incontinence; urinary urge incontinence; overactive bladder; cystitis; nephritis; pancreatitis; uveitis; splanchnopathy; ischemia; apoplexy; dystonia; obesity; septicemia; and pruritus The literature and publications cited in this Description are hereby incorporated by reference in this Description in their entirety regardless of their objects. This specification also encompasses the disclosure of the claims, specification and drawings of each of Japanese Patent Application No. 2017-108017 (filed May 31, 2017, Japan) and U.S. Provisional Application No. 62/512,775 (filed May 31, 2017, US) on which the priority claim of the present application is based.

Example

Next, the present invention is explained in more detail below based on examples and test examples, but these examples are merely implementations that do not limit the present invention, and may be varied without departing from the scope of the present invention.

"Room temperature" in the examples means a temperature of normally 1° C. to 30° C. (as stipulated by the Japanese Pharmacopoeia).

Commercial solvents were used without purification for crystallization in the examples.

X-ray powder diffraction analysis was performed using a D8 Discover with GADDS CS (Bruker Corporation) by the Bragg-Brentano method (X-ray source: 40 kV, 40 mA, Wavelength: 1.5418 Å (CuK alpha), Camera length: 250 mm, temperature: room temperature, Phi Position: 0 degrees, Exposure time: 2 minutes, Theta 1: 7 degrees, Theta 2: 7 degrees).

Differential scanning calorimetry (DSC) measurement was performed using a DSC6220 differential scanning calorimeter (Seiko Instruments Inc.) within a range of 50° C. to 300° C. at a ramp rate of 10° C./minute. FT-IR measurement was performed using an FT-720 (Horiba, Ltd.) by the KBr method. The microscopic images were measured with an MTFP82HT (Mettler-Toledo International Inc.).

Chemical purity measurement was performed using a Develosoil ODS-HG-5 column (size 4.6×150 mm). The mobile phase was acetonitrile:water=1:1.

(Reference Example) Synthesis of (E)-2-(7-trifluoromethyl-chroman-4-ylidene)-N-((7R)-7-hydroxy-5,6,7,8-tetrahydronaphthalen-1-yl)acetamide The (E)-2-(7-trifluoromethyl-chroman-4-ylidene)-N-(7-hydroxy-5,6,7,8-tetrahydronaphthalen-1-yl)acetamide (Compound A) of Example 70 of WO 2007/010383 is subjected to optical resolution by preparative chromatography (column: Daicel Chemical Industries, Ltd. Chiralpak AD-H, 10 cm ID×25 cm, solvent methanol:acetonitrile 9:1, flow rate 189 mL/min, column temperature 40° C., sample concentration 7 g/L (EtOH)) to obtain the Compound (1).

(Example 1) Type I Crystal of (E)-2-(7-trifluoromethyl-chroman-4-ylidene)-N-((7R)-7-hydroxy-5,6,7,8-tetrahydronaphthalen-1-yl)acetamide The Compound (1) (165.2 g) was dissolved under heating at 60° C. to 70° C. in acetone/ethanol (99.5%) (1/1, 1.6 L). Water (600 mL) was added under stirring, and the mixture was cooled to room temperature under stirring. The precipitated crystals were filtered out, and washed sequentially with ethanol/water (1/1) and water. The result crystals were dried under reduced pressure to obtain white crystals (146.7 g) as the type I crystal.

Figure 4:
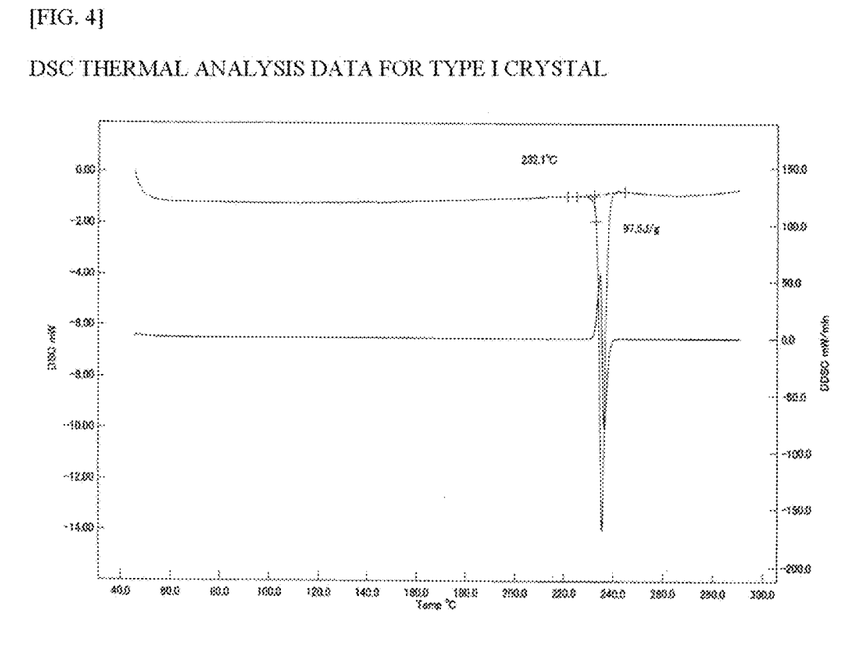
FIG. 4 shows DSC thermal analysis data for the type I crystal of the Compound (1) of Example 1.

FIG. 1 shows measurement results from x-ray powder diffraction of the type I crystal, the peaks of the type I crystal are shown in Table 2, and the characteristic peaks are shown in Table 3. FIG. 2 shows a microscopic photograph of the type I crystal. The FT-IR spectrum data for the type I crystal are shown in FIG. 3 and Table 4. FIG. 4 shows the DSC thermal analysis data for the type I crystal. In the DSC thermal analysis data, no obvious temperature-dependent endothermic/exothermic peak appears between room temperature and the melting point.

TABLE 2

| X-ray powder analysis data for type I crystal | |
|---|---|
| 2θ (°) | Relative intensity (%) |
| 7.9 | 9.9 |
| 8.9 | 11.9 |
| 10.3 | 11.7 |
| 12.0 | 8.8 |
| 15.8 | 83.6 |
| 16.4 | 31.4 |
| 17.2 | 22.7 |
| 17.6 | 11.3 |

TABLE 2-continued

X-ray powder analysis data for type I crystal

| 2θ (°) | Relative intensity (%) |
|---|---|
| 18.3 | 19.5 |
| 19.5 | 34.8 |
| 19.9 | 23.7 |
| 20.8 | 26.4 |
| 21.6 | 65.9 |
| 23.9 | 100 |
| 24.6 | 19.3 |
| 25.0 | 27.9 |
| 26.3 | 16.7 |
| 26.7 | 20.7 |
| 27.7 | 19.6 |
| 28.6 | 14.8 |
| 29.5 | 10.6 |
| 31.4 | 11.4 |
| 32.4 | 18.0 |
| 33.2 | 10.7 |
| 33.8 | 9.1 |
| 34.8 | 9.6 |

TABLE 3

X-ray powder analysis data for type I crystal (characteristic data)

| 2θ (°) | Relative intensity (%) |
|---|---|
| 7.9 | 9.9 |
| 10.3 | 11.7 |
| 15.8 | 83.6 |
| 16.4 | 31.4 |
| 17.2 | 22.7 |
| 19.5 | 34.8 |
| 19.9 | 23.7 |
| 21.6 | 65.9 |
| 23.9 | 100 |
| 25.0 | 27.9 |
| 26.7 | 20.7 |

TABLE 4

FT-IR spectrum data for type I crystal
Type I Crystal

| Wavenumbers (cm$^{-1}$) | Transmittance (%) |
|---|---|
| 3284 | 22.3 |
| 1639 | 11.0 |
| 1614 | 8.7 |
| 1525 | 9.6 |
| 1435 | 6.4 |
| 1336 | 2.1 |
| 1140 | 7.3 |
| 1120 | 3.7 |
| 1080 | 13.6 |
| 1049 | 12.5 |
| 891 | 35.3 |
| 825 | 33.3 |

Example 2

The Compound (1) (200 mg) was dissolved under heating at 60° C. in acetone/ethanol (99.5%) (7/3, 15 mL), and water (14 mL) was added under heating for 20 minutes. This was then cooled to room temperature. The precipitated crystals were filtered out, and washed sequentially with ethanol/water (1/1) and water. The resulting crystals were dried under reduced pressure to obtain white crystals (188 mg) as the type I crystal.

When the crystals were measured by the x-ray powder diffraction, the characteristic peaks of the type I crystal as shown in Table 3 were observed.

(Example 3) Type II Crystal of (E)-2-(7-trifluoromethyl-chroman-4-ylidene)-N-((7R)-7-hydroxy-5,6,7,8-tetrahydronaphthalen-1-yl)acetamide The Compound (1) (40.0 g) was dissolved in ethyl acetate/methanol (1440 mL/400 mL), and concentrated under reduced pressure. Ethyl acetate was added, and the suspended solution was filtered and then dried under reduced pressure to obtain white crystals (33.6 g) as the type II crystal.

Figure 8:
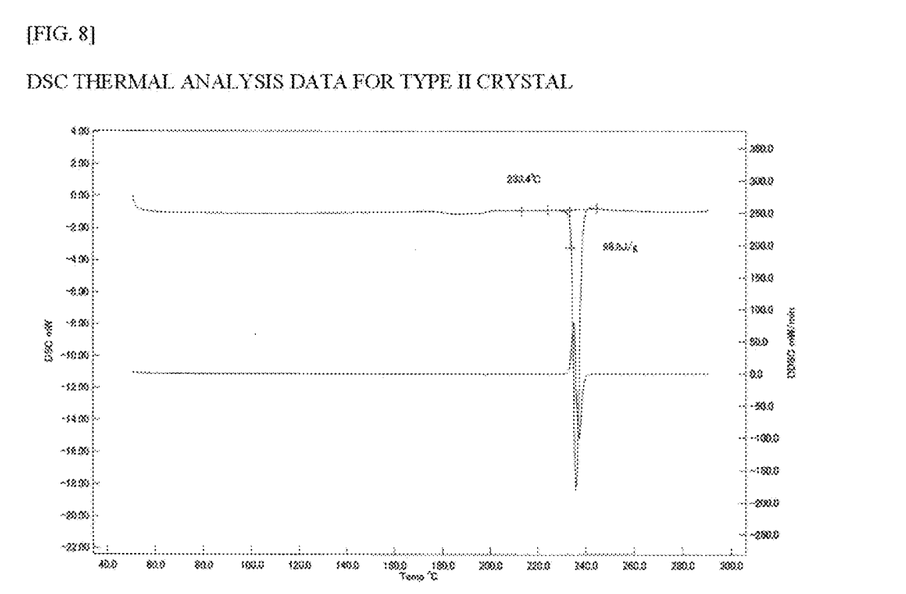
FIG. 8 shows DSC thermal analysis data for the type II crystal of the Compound (1) of Example 3.

The x-ray powder diffraction measurement results for the type II crystal are shown in FIG. 5, and the characteristic peaks of the type II crystal in Table 5. FIG. 6 shows a microscopic photograph of the crystal. The FT-IR spectrum data for the crystal are shown in FIG. 7 and Table 6. The DSC thermal analysis data for the crystal are shown in FIG. 8.

In the DSC thermal analysis, some heat absorption was confirmed near 170 to 200° C., and a change in crystal form was confirmed under the microscope.

TABLE 5

X-ray powder analysis data for type II crystal

| 2θ (°) | Relative intensity (%) |
|---|---|
| 10.5 | 9.7 |
| 12.2 | 23.7 |
| 12.7 | 16.0 |
| 16.1 | 15.0 |
| 17.1 | 19.3 |
| 18.4 | 17.8 |
| 19.1 | 11.7 |
| 20.6 | 13.9 |
| 22.4 | 100 |
| 23.8 | 40.1 |

TABLE 6

FT-IR spectrum data for type II crystal
Type II Crystal

| Wavenumbers (cm$^{-1}$) | Transmittance (%) |
|---|---|
| 3350 | 43.9 |
| 1651 | 30.5 |
| 1618 | 39.6 |
| 1529 | 43.0 |
| 1435 | 24.8 |
| 1336 | 15.2 |
| 1142 | 30.0 |
| 1124 | 23.1 |
| 1078 | 33.5 |
| 1047 | 38.0 |
| 883 | 57.1 |
| 814 | 55.9 |

(Example 4) Type III Crystal of (E)-2-(7-trifluoromethyl-chroman-4-ylidene)-N-((7R)-7-hydroxy-5,6,7,8-tetrahydronaphthalen-1-yl)acetamide The Compound (1) (1.5 g) was dissolved in dimethylsulfoxide (15 mL). Dimethylsulfoxide/water (1/2, 22.5 mL)

was added under stirring at room temperature in three additions, and the mixture was stirred for 30 minutes. The produced crystals were filtered out, and the resulting crystals were washed with ethanol/water (1/4, 3 mL, 2 times), water (3 mL, 2 times) and ethanol (3 mL). The crystals were dried under reduced pressure for 2 hours at 40° C. to obtain white crystals (1.41 g) as the type III crystal.

The powder diffraction measurement results for the type III crystal are shown in FIG. 9. The characteristic peaks of the type III crystal are shown in Table 7.

TABLE 7

X-ray powder analysis data for type III crystal

| 2θ (°) | Relative intensity (%) |
|---|---|
| 6.9 | 18.1 |
| 13.0 | 34.1 |
| 16.6 | 21.7 |
| 17.6 | 41.4 |
| 19.9 | 19.9 |
| 20.6 | 42.1 |
| 21.3 | 16.9 |
| 22.2 | 100 |
| 24.0 | 63.9 |
| 27.2 | 27.2 |
| 27.8 | 26.4 |

(Experimental Example 1) Solvent Suspension Test of Crystal Form Mixture

The respective crystal forms (type I crystal, type II crystal) of (E)-2-(7-trifluoromethyl-chroman-4-ylidene)-N-((7R)-7-hydroxy-5,6,7,8-tetrahydronaphthalen-1-yl)acetamide obtained by crystallization were mixed in equal amounts to prepare a crystal form mixture, and this crystal form mixture was mixed with various solvents (acetonitrile, ethanol or 2-propanol), and suspended (formed a slurry) and stirred for 5 days at 25° C. The crystals were filtered out, and it was confirmed from the x-ray powder diffraction pattern that all were type I crystals.

These results showed clearly that the type I crystal of the invention was thermodynamically stable in suspension under conditions of 25° C. Consequently, by using the type I crystal of the present invention in a pharmaceutical product, it is possible to prevent crystal transitions ahead of time in the pharmaceutical manufacturing process, and maintain the quality of the active pharmaceutical ingredient and pharmaceutical product.

(Experimental Example 2) Storage Stability Test

The type I and type II crystals of (E)-2-(7-trifluoromethyl-chroman-4-ylidene)-N-((7R)-7-hydroxy-5,6,7,8-tetrahydronaphthalen-1-yl)acetamide obtained by crystallization (about 30 mg) were placed in glass bottles, and stored under various conditions. After the end of the storage period, the samples were removed, their chemical purities were measured by high performance liquid chromatography, and the crystal forms were confirmed by x-ray powder analysis. The results are shown in Table 8.

TABLE 8

Powder stability

| Crystal | Storage conditions | Chemical purity (%) | Crystal form |
|---|---|---|---|
| Type I crystal | Before test | >99.9 | Type I |
| | 25° C./60% RH, 1 month, sealed | >99.9 | Type I |
| | 40° C./75% RH, 1 month, sealed | >99.9 | Type I |
| | 60° C., 1 month, sealed | >99.9 | Type I |
| Type II crystal | Before test | >99.9 | Type II |
| | 25° C./60% RH, 1 month, sealed | >99.9 | Type II |
| | 40° C./75% RH, 1 month, sealed | >99.9 | Type II |
| | 60° C., 1 month, sealed | >99.9 | Type II |

(Experimental Example 3) Long-Term Storage Stability Test

The type I crystal of (E)-2-(7-trifluoromethyl-chroman-4-ylidene)-N-((7R)-7-hydroxy-5,6,7,8-tetrahydronaphthalen-1-yl)acetamide obtained by crystallization (400 mg) was placed in a double LDPE (low density polyethylene) bag, placed in a fiber drum, and stored under the conditions described in Table 9. After the end of the storage period, the samples were removed, their chemical purities were measured by high performance liquid chromatography, and the crystal forms were confirmed by x-ray powder analysis. The results are shown in Table 9.

TABLE 9

Powder stability

| Crystal | Storage conditions | Chemical purity (%) | Crystal form |
|---|---|---|---|
| Type I crystal | Before test | >99.9 | Type I |
| | 25° C./60% RH, 3 months, sealed | >99.9 | — |
| | 25° C./60% RH, 6 months, sealed | >99.9 | Type I |
| | 25° C./60% RH, 13 months, sealed | >99.9 | Type I |
| | 25° C./60% RH, 24 months, sealed | >99.9 | Type I |
| | 25° C./60% RH, 36 months, sealed | >99.9 | Type I |
| | 25° C./60% RH, 48 months, sealed | >99.9 | Type I |

The results of (Experimental Example 2) and (Experimental Example 3) showed that the type I crystal of the invention was chemically and physically stable throughout the test period. Moreover, no moisture absorption by the type I crystal was observed during that period.

Consequently, the quality of the drug substance is maintained within the standard over a long period of time, and throughout this period it can be easily worked into a pharmaceutical product and used as a pharmaceutical preparation.

(Experimental Example 4) Photostability Test

The type I crystal and type II crystal (about 2 g each) of (E)-2-(7-trifluoromethyl-chroman-4-ylidene)-N-((7R)-7-hydroxy-5,6,7,8-tetrahydronaphthalen-1-yl)acetamide obtained by crystallization were placed in glass dish-shaped containers, and subjected to photostability testing in accordance with ICH Q1B (Guidelines for photostability testing of new drugs and new formulations) (the photostability test samples are stored under a separate lamp emitting visible light and UV-A light, and total exposure is set to 1.2 million lux hours and 200 watt hours/m$^2$ or more at 25° C.; the 10-day test is shown as 1ICH). After completion of the test, each sample was removed, its chemical purity was measured by high performance liquid chromatography, and the crystal form was confirmed by x-ray powder analysis. The results are shown in Table 10.

TABLE 10

Photostability

| Crystal | Test conditions | Chemical purity (%) | Crystal form |
| --- | --- | --- | --- |
| Type I crystal | Before test | >99.9 | Type I crystal |
|  | 1ICH | >99.9 | Type I crystal |
| Type II crystal | Before test | >99.9 | Type II crystal |
|  | 1ICH | 98.2 | Type II crystal |

These results showed clearly that the type II crystal of the invention was unstable with respect to light, while the type I crystal had extremely high chemical and physical stability. Consequently, the type I crystal is easy to handle as an active pharmaceutical ingredient during pharmaceutical manufacturing, and is suitable to pharmaceutical ingredients and pharmaceutical preparations. Moreover, since it does not undergo photodecomposition or structural isomerization of the compound or any decrease in biological activity, its bioavailability is not affected, its formulation properties as a pharmaceutical product remain stable, and it can be stored for a long period of time.

The Compound (1) of the present invention has a chroman-4-ylidene structure, and there is concern that this structure can transition to a 2H-chromene structure under light exposure. A decrease of bioactivity is also a concern under these circumstances.

FORMULATION EXAMPLES

Examples of the pharmaceutical composition of the invention are given below.

| Formulation Example 1: Tablets | |
| --- | --- |
| Type I crystal of Example 1 | 100 g |
| Lactose | 137 g |
| Crystalline cellulose | 30 g |
| Hydroxypropyl cellulose | 15 g |
| Carboxymethyl starch sodium | 15 g |
| Magnesium stearate | 3 g |

The above ingredients are weighed and mixed uniformly. The resulting mixture is compressed to prepare a tablet having a weight of 150 mg.

| Formulation Example 2: Capsules | |
| --- | --- |
| Type I crystal of Example 1 | 50 g |
| Lactose | 435 g |
| Magnesium stearate | 15 g |

The above ingredients are weighed and then mixed homogeneously. Subsequently, 300 mg of the resulting mixture is filled in an appropriate hard capsule with a capsule enclosing device, thus allowing a capsule to be prepared.

| Formulation Example 3: Capsules | |
| --- | --- |
| Type I crystal of Example 1 | 100 g |
| Lactose | 63 g |
| Corn starch | 25 g |
| Hydroxypropyl cellulose | 10 g |
| Talc | 2 g |

The above ingredients are weighed. Type I crystal of Example 1, lactose, and corn starch are then mixed homogeneously, and an aqueous solution of hydroxypropyl cellulose is added to the mixture. Granules are produced by a wet granulation method. Talc is then homogeneously mixed with the granules. Subsequently, 200 mg of the resulting mixture is filled in an appropriate hard capsule, thus allowing a capsule to be prepared.

| Formulation Example 4: Powder | |
| --- | --- |
| Type I crystal of Example 1 | 200 g |
| Lactose | 790 g |
| Magnesium stearate | 10 g |

The above ingredients are weighed and then mixed homogeneously. Thus, 20% powder medicine is prepared.

INDUSTRIAL APPLICABILITY

Because it has excellent TRPV1 antagonism, the crystal of the invention can provide a preventative and/or therapeutic agent that is clinically useful for diseases such as pain.

Moreover, the crystal of the invention is excellent in at least one feature selected from the group consisting of storage stability, photostability and thermodynamic stability, can preferably be obtained with industrially high reproducibility, yield and purity, and is useful as a crystal of an active pharmaceutical ingredient. Moreover, preferably the crystal producing method of the invention can provide this crystal easily, with good yield, reproducibly and industrially, and is also useful for obtaining a stable supply for pharmaceutical manufacture. Moreover, a crystal of the Compound (1) such as that described above is useful because it allows an excellently stable pharmaceutical composition to be provided.

Some specific embodiments of the present invention were explained in detail above, but a person skilled in the art can make various modifications and changes thereto to the extent that these do not effectively deviate from the teachings and advantages of the invention. Consequently, such modifications and changes are all included within the spirit and scope of the present invention as presented in the Claims.

What we claimed is:

1. A type I crystal of (E)-2-(7-trifluoromethyl-chroman-4-ylidene)-N-((7R)-7-hydroxy-5,6,7,8-tetrahydronaphthalen-1-yl)acetamide having characteristic peaks at least at diffraction angles (2θ) of about 7.9, about 10.3, about 15.8, about 16.4, about 17.2, about 19.5, about 19.9, about 21.6, about 23.9, about 25.0 and about 26.7(°) in x-ray powder diffraction (Cu-Kα).

2. A type I crystal of (E)-2-(7-trifluoromethyl-chroman-4-ylidene)-N-((7R)-7-hydroxy-5,6,7,8-tetrahydronaphthalen-1-yl)acetamide having characteristic peaks at diffraction angles (2θ) of about 7.9, about 8.9, about 10.3, about 12.0, about 15.8, about 16.4, about 17.2, about 17.6, about 18.3, about 19.5, about 19.9, about 20.8, about 21.6, about 23.9, about 24.6, about 25.0, about 26.3, about 26.7, about 27.7, about 28.6, about 29.5, about 31.4, about 32.4, about 33.2, about 33.8 and about 34.8 (°) in x-ray powder diffraction (Cu-Kα).

3. A type I crystal of (E)-2-(7-trifluoromethyl-chroman-4-ylidene)-N-((7R)-7-hydroxy-5,6,7,8-tetrahydronaphthalen-1-yl)acetamide, characterized by an x-ray powder diffraction pattern shown in FIG. 1.

4. The type I crystal according to any one of claims 1 to 3, having an extrapolated melting point onset temperature of 232° C. in differential scanning calorimetry measurement (DSC measurement).

5. The type I crystal according to any one of claims 1 to 3, having a needle-shaped crystal morphology.

6. A method for producing the type I crystal of (E)-2-(7-trifluoromethyl-chroman-4-ylidene)-N-((7R)-7-hydroxy-5,6,7,8-tetrahydronaphthalen-1-yl)acetamide according to any one of claims 1 to 3, the method comprising a step of dissolving (E)-2-(7-trifluoromethyl-chroman-4-ylidene)-N-((7R)-7-hydroxy-5,6,7,8-tetrahydronaphthalen-1-yl)acetamide under heating with a solvent selected from alcohol solvents, and mixed solvents of alcohol solvents and acetone, adding water under heating and stirring, and then cooling the mixed solution containing water with stirring to room temperature to obtain crystals.

7. A pharmaceutical composition containing the crystal according to any one of claims 1 to 3 as an active ingredient.

8. The pharmaceutical composition according to claim 7, which is a TRPV1 antagonist.

9. The pharmaceutical composition according to claim 7, which is a preventative and/or therapeutic agent for pain.

10. A method of manufacturing a pharmaceutical composition comprising combining the crystal according to any one of claims 1 to 3 with pharmaceutically acceptable additives.

* * * * *